Jan. 22, 1974 B. J. MACHIN Plant Pat. 3,451
CHRYSANTHEMUM PLANT
Filed Dec. 27, 1971
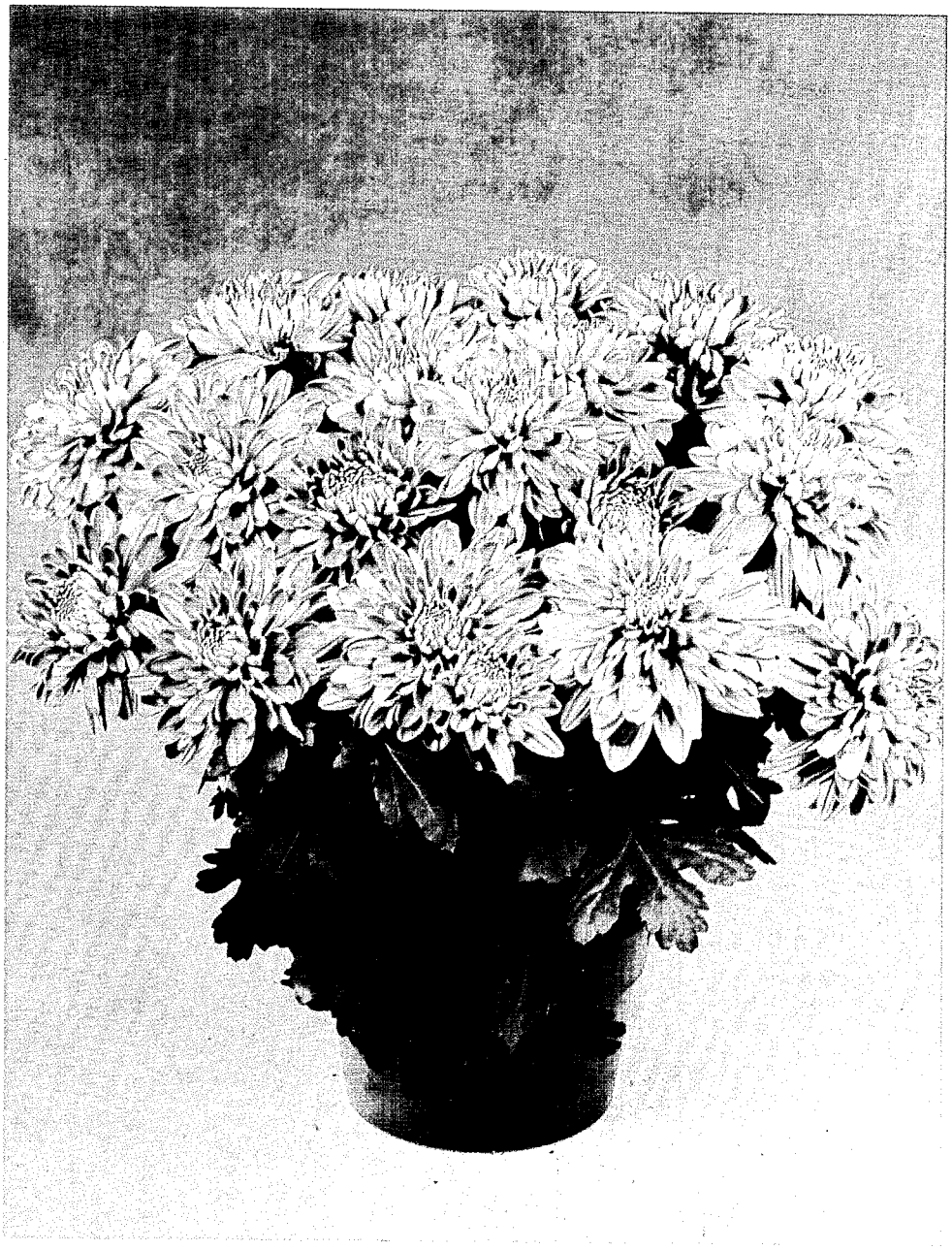

United States Patent Office

Plant Pat. 3,451
Patented Jan. 22, 1974

3,451
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,837
Int. Cl. A01h 5/00
U.S. Cl. Plt.—81 1 Claim This invention releates to a new and distinctive variety of *Chrysanthemum morifolium* Bailey, pot type, known as Aramis.

Aramis is a seedling originated by me from a cross made in 1966 between the unpatented variety Redcap and the unpatented variety Frolic, the former being the seed parent, and the latter being the pollen parent.

The variety Aramis resulted from an extensive breeding program with the object of producing improved varieties for year round pot chrysanthemum production with more uniformity and improved response as compared with the existing varieties.

Aramis is distinguished from its seed parent Redcap in the following particulars:

(1) Flower color is mauve pink rather than crimson red.
(2) Foliage is larger.
(3) Habit of growth is stronger and more vigorous.

Aramis is distinguished from its pollen parent Frolic in the following particulars:

(1) It has a larger more decorative type of flower less tightly incurving in nature.
(2) It has a more vigorous and stronger growth habit.

Aramis has the following improved characteristics over the Princess Anne varieties, which are the most closely similar varieties with which I am familiar:

(1) It has a shorter internode length and it is thus easier to control height of plant by day length or chemical control measures.
(2) Although flowers are smaller, form is improved and there are more petals, and more flowers per plant are obtained.
(3) Response is more uniform in poor winter light conditions.

In color Aramis resembles Bravo. As compared with Bravo it takes 10 days longer to flower in short day conditions, but has a much improved flower form and produces a plant of better habit.

Asexual reproduction of this new variety Aramis, as performed in Sussex, England, by rooting vegetative shoots, shows that the above characteristics are fixed and come true ot type through succeeding generations.

The accompanying drawing shows a typical flower of my new variety depicted in color as nearly true as it is reasonably possible to make the same in a color illustration of this character.

The following is a detailed description of the new variety Aramis with color terminology in accordance with the Royal Horticultural Society color chart, hereinafter referred to as RHS.

Genus: Chrysanthemum
Species: *Morifolium* Bailey
Type: Pot
Class: Decorative
Breeding: The original seedling resulted from a cross between the variety Redcap and the variety Frolic, the former being the seed parent, the latter being the pollen parent. The cross was made in 1966 at Frampton's Nurseries Ltd., Forbridge Nursery, Chichester, Sussex, England.
Propagation: Holds its distinguishing characteristics through suceeding propagations by rooting vegetative shoots.
Flower: When grown in Sussex, England, in 3½ inch pots and pinched, up to 6 flowers per plant are formed. When five plants are planted per 5 inch pot, 4 to 5 flowers are borne on each plant.
Bloom:
*Size.*—Average diameter is 8 to 10 cm. when fully open.
*Petalage.*—Decorative with approximately 250 ray petals and five disc petals.
*Form.*—Decorative.
*Petals.*—Medium length, broad, overlapping, blunt, flat and of medium texture.
Color of open bloom:
Inner face of fully expanded petals, RHS 70B. Outer face of fully expanded petals, RHS 73D. Inner face of yuong petals, RHS 70B. Outer face of young petal, RHS 73D.
Response Group: 10 weeks.
Temperature tolerance: 55–60° F. at night.
Plant: Stocky, well branched habit of growth.
Foliage:
Medium quality; average internode length 1½ to 2 cms. Medium size. Color, RHS 137C, and has medium texture.
Stem: Thick and strong.
Color: 145C at flowering.

I claim:

1. A new and distinct variety of *Chrysanthemum morifolium* Bailey, substantially as herein shown and described, characterized particularly as to novelty by the unique combination of purple color, short internode length, and uniform response time in poor winter light conditions.

No references cited.

ROBERT E. BAGWILL, Primary Examiner